United States Patent
Jamal et al.

(10) Patent No.: US 11,776,524 B2
(45) Date of Patent: Oct. 3, 2023

(54) ELECTROMYOGRAPHY SIGNAL DETECTION DEVICE

(71) Applicants: Hyundai Motor Company, Seoul (KR); Kia Corporation, Seoul (KR)

(72) Inventors: Muhammad Zahak Jamal, Yongin-si (KR); Dong Jin Hyun, Suwon-si (KR); Dong Hyun Lee, Uiwang-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 184 days.

(21) Appl. No.: 17/443,510

(22) Filed: Jul. 27, 2021

(65) Prior Publication Data

US 2022/0076654 A1    Mar. 10, 2022

(30) Foreign Application Priority Data

Sep. 4, 2020    (KR) .......................... 10-2020-0113256

(51) Int. Cl.
*A61B 5/389* (2021.01)
*G10K 11/178* (2006.01)

(52) U.S. Cl.
CPC ........ *G10K 11/17813* (2018.01); *A61B 5/389* (2021.01); *G10K 11/17823* (2018.01); *G10K 11/17854* (2018.01); *G10K 2210/3016* (2013.01)

(58) Field of Classification Search
CPC ........ A61B 5/389; A61B 5/7225; A61B 5/725
See application file for complete search history.

(56) References Cited

FOREIGN PATENT DOCUMENTS

| KR | 20180012891 A |   | 2/2018 |
|---|---|---|---|
| KR | 20200044406 A | * | 4/2020 |

* cited by examiner

*Primary Examiner* — Kile O Blair
(74) *Attorney, Agent, or Firm* — Slater Matsil, LLP

(57) ABSTRACT

An embodiment electromyography signal detection device includes a noise signal obtaining device configured to obtain a noise signal of an unknown reference frequency at a periphery of a user, an electromyography signal acquisition device configured to measure an electromyography signal from the user, and a controller configured to remove a noise signal included in the electromyography signal of the user based on the obtained noise signal of the unknown reference frequency.

20 Claims, 13 Drawing Sheets

ELECTROMYOGRAPHY SIGNAL DETECTION DEVICE

CROSS-REFERENCE TO RELATED APPLICATIONS

This application claims the benefit of Korean Patent Application No. 10-2020-0113256, filed on Sep. 4, 2020, which application is hereby incorporated herein by reference.

TECHNICAL FIELD

The present disclosure relates to an electromyography signal detection device.

BACKGROUND

In general, an electromyography (EMG) signal contains various noise signals depending on surrounding environments and measurement methods. The noise signals may be generated by power line interference (e.g., 50 Hz and harmonics thereof or 60 Hz and harmonics thereof), motion artifacts, and direct current (DC) noise.

Because the electromyography signal includes noise signals capable of causing an error in a process of diagnosing a user's condition, there is a need for a process of removing the noise signals from the electromyography signal.

Conventional electromyography (EMG) signal detection technologies analyze the measured electromyography signal to investigate noise patterns and remove noise signals from the real time EMG signal using traditional methods to acquire the final electromyography output.

To extract the noise signal from the measured electromyography signal, the conventional method needs to include a database, in which information about noise signals is recorded in advance, which causes an increase in implementation complexity.

The matters described in this Background are intended to enhance the understanding of the background of the present disclosure and may include matters that are not the prior art already known to those of ordinary skill in the art.

SUMMARY

The present disclosure relates to an electromyography signal detection device. Particular embodiments relate to a technology for removing a noise signal from an electromyography signal based on an adaptive filter.

Embodiments of the present disclosure can solve problems occurring in the prior art while advantages achieved by the prior art are maintained intact.

An embodiment of the present disclosure provides a device and method for detecting an electromyography signal that may detect an electromyography signal with high accuracy by obtaining a noise signal of a reference frequency at a periphery of a user and removing the noise signal included in the user's electromyography signal in real time in an adaptive filtering scheme based on the obtained noise signal.

Embodiments of the present disclosure are not limited to the above-mentioned embodiment, and other features and advantages of embodiments of the present disclosure that are not mentioned will be understood from the following description, and it will be apparently understood from embodiments of the present disclosure. In addition, it will be easily understood that the features and advantages of embodiments of the disclosure are realized by means and combinations described in the appended claims.

The technical problems that may be solved by embodiments of the present inventive concept are not limited to the aforementioned problems, and any other technical problems not mentioned herein will be clearly understood from the following description by those skilled in the art to which the present disclosure pertains.

According to an embodiment of the present disclosure, an electromyography signal detection device may include a noise signal obtaining device which acquires a noise signal of a reference frequency at a periphery of a user, an electromyography signal acquisition device which measures an electromyography signal from the user, and a controller which removes a noise signal included in the electromyography signal of the user based on the obtained noise signal.

In an embodiment of the present disclosure, the controller may remove the noise signal included in the electromyography signal of the user by using an adaptive filter.

In an embodiment of the present disclosure, the noise signal obtaining device may obtain the noise signal based on a scheme which uses a wire which serves the purpose of an antenna, a second scheme which uses an additional electrode in contact with the skin of the user, and a third scheme which combines the first scheme and the second scheme.

In an embodiment of the present disclosure, the noise signal obtaining device may obtain the ambient noise signal with an unknown reference frequency, which is capacitively coupled to the wire, through an arbitrary capacitance of an unknown value.

In an embodiment of the present disclosure, the noise signal obtaining device may receive the obtained noise signal from the wire through an analog-digital converter (ADC) channel.

In an embodiment of the present disclosure, the noise signal obtaining device may obtain the ambient noise signal with an unknown reference frequency, which is capacitively coupled to the skin of the user, through an arbitrary capacitance of an unknown value by attaching an additional electrode to the user's skin.

In an embodiment of the present disclosure, the noise signal obtaining device may receive the obtained noise signal from the electrode through an ADC channel.

In an embodiment of the present disclosure, the noise signal obtaining device may obtain the final ambient noise signal with an unknown reference frequency by superimposing the noise signal capacitively coupled to the wire and the noise signal capacitively coupled to the skin of the user.

In an embodiment of the present disclosure, the noise signal obtaining device may receive the final noise signal through an ADC channel.

According to an embodiment of the present disclosure, a method of detecting an electromyography signal may include obtaining a noise signal with an unknown reference frequency at the periphery of a user by a noise signal obtaining device, measuring the electromyography signal from the user by an electromyography signal acquisition device, and removing a noise signal included in the electromyography signal of the user based on the obtained noise signal by a controller.

In an embodiment of the present disclosure, the removing of the noise signal included in the electromyography signal of the user may include removing the noise signal included in the electromyography signal of the user by using an adaptive filter.

In an embodiment of the present disclosure, the obtaining of the noise signal with an unknown reference frequency may include obtaining the noise signal based on a first scheme which uses a wire as an antenna, a second scheme using an additional electrode in contact with a skin of the user, and a third scheme obtained by combining the first scheme and the second scheme.

In an embodiment of the present disclosure, the obtaining of the ambient noise signal with an unknown reference frequency may involve acquiring the noise signal capacitively coupled to the wire through an arbitrary capacitance of an unknown value.

In an embodiment of the present disclosure, the obtaining of the noise signal of the reference frequency may further include receiving the obtained noise signal from the wire through an ADC channel.

In an embodiment of the present disclosure, the obtaining of the ambient noise signal with an unknown reference frequency may involve acquiring the noise signal capacitively coupled to the skin of the user using an additional electrode through an arbitrary capacitance of an unknown value.

In an embodiment of the present disclosure, the obtaining of the noise signal of the reference frequency may further include receiving the obtained noise signal from the electrode through an ADC channel.

In an embodiment of the present disclosure, the obtaining of the ambient noise signal with an unknown reference frequency may include obtaining a final noise signal obtained by superimposing the noise signal capacitively coupled to the wire and the noise signal capacitively coupled to the skin of the user.

In an embodiment of the present disclosure, the obtaining of the noise signal of an unknown reference frequency may further include receiving the final noise signal through an ADC channel.

BRIEF DESCRIPTION OF THE DRAWINGS

The above and other objects, features and advantages of embodiments of the present disclosure will be more apparent from the following detailed description taken in conjunction with the accompanying drawings, in which.

DETAILED DESCRIPTION OF ILLUSTRATIVE EMBODIMENTS

Figure 1:
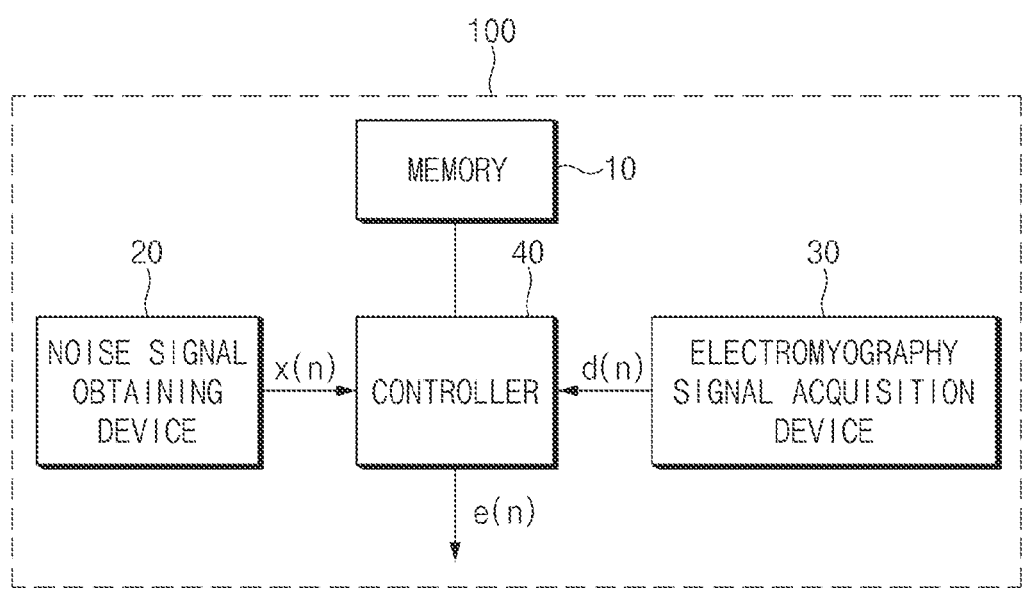
FIG. 1 is a block diagram of an electromyography signal detection device according to an embodiment of the present disclosure.

Hereinafter, some embodiments of the present disclosure will be described in detail with reference to the example drawings. In adding the reference numerals to the components of each drawing, it should be noted that the identical or equivalent component is designated by the identical numeral even when they are displayed on other drawings. Further, in describing the embodiments of the present disclosure, a detailed description of well-known features or functions will be omitted in order not to unnecessarily obscure the gist of the present disclosure.

In describing the components of the embodiments according to the present disclosure, terms such as first, second, "A", "B", (a), (b), and the like may be used. These terms are merely intended to distinguish one component from another component, and the terms do not limit the nature, sequence or order of the constituent components. Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art, and are not to be interpreted as having ideal or excessively formal meanings unless clearly defined as having such in the present application.

FIG. 1 is a block diagram of an electromyography signal detection device according to an embodiment of the present disclosure.

As illustrated in FIG. 1, an electromyography signal detection device 100 may include a memory 10, a noise signal obtaining device 20, an electromyography signal acquisition device 30, and a controller 40. At this time, in accordance with the method of operating the electromyography signal detection device 100 according to an embodiment of the present disclosure, each of the components may be implemented as one device after being coupled with one another or a part of components may be omitted.

Referring to each of the components, first of all, the memory 10 may store various logics, algorithms, and programs that are required in a process of obtaining a noise signal of a reference frequency at a periphery of a user and removing the noise signal included in the user's electromyography signal through an adaptive filtering scheme based on the obtained noise signal.

The memory 10 may include at least one type of a storage medium among a flash memory type of a memory, a hard disk type of a memory, a micro type of a memory, and a card type (e.g., a Secure Digital (SD) card or an eXtream Digital (XD) Card) of a memory, a Random Access Memory (RAM) type of a memory, a Static RAM (SRAM) type of a memory, a Read-Only Memory (ROM) type of a memory, a Programmable ROM (PROM) type of a memory, an Electrically Erasable PROM (EEPROM) type of a memory, a Magnetic RAM (MRAM) type of a memory, a magnetic disk type of a memory, or an optical disc type of a memory.

The noise signal obtaining device 20 may obtain a noise signal with an unknown reference frequency at a periphery of the user. The noise signal obtaining device 20 may obtain a noise signal by using a first scheme which uses a wire as an antenna, a second scheme using an electrode in contact with a human body (the user's skin), and a third scheme obtained by combining the first scheme and the second scheme.

The electromyography signal acquisition device 30 may measure an electromyography signal from the user. The electromyography signal acquisition device 30 may measure an electromyography signal in a variety of generally well-known schemes, and is not limited to any one scheme.

The controller 40 performs overall control such that each of the components is capable of normally performing functions of the components. The controller 40 may be implemented in the form of hardware, may be implemented in the form of software, or may be implemented in the form of the combination of hardware and software. Favorably, the controller 40 may be implemented as a microprocessor, but is not limited thereto.

In particular, the controller 40 may perform various controls in a process of obtaining a noise signal of a reference frequency at a periphery of the user and removing the noise signal included in the user's electromyography signal through an adaptive filtering scheme, based on the obtained noise signal.

Figure 2:
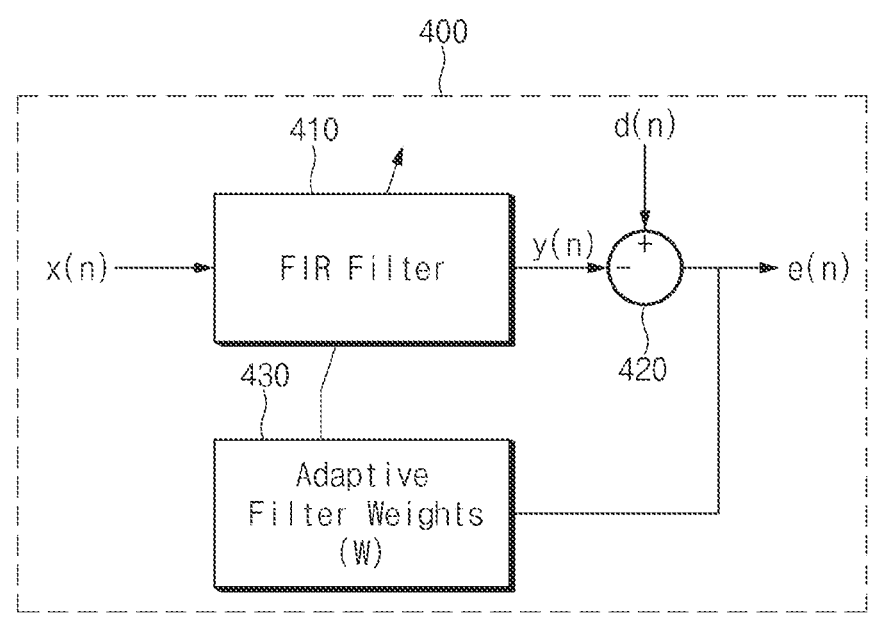
FIG. 2 is a structural diagram of an adaptive filter included in a controller of an electromyography signal detection device according to an embodiment of the present disclosure.

The controller 40 may include an adaptive filter as shown in FIG. 2.

FIG. 2 is a structural diagram of an adaptive filter included in a controller of an electromyography signal detection device according to an embodiment of the present disclosure.

As illustrated in FIG. 2, an adaptive filter 400 included in the controller 40 may include a finite impulse response (FIR) filter 410, a subtractor 420, and adaptive filter weights 430.

In FIG. 2, $d(n)$ may be an electromyography signal measured by the electromyography signal acquisition device 30, and may include a noise signal generated by a noise component of 50 Hz and harmonics thereof, or a noise component of 60 Hz and harmonics thereof, or other noise components distributed in the frequency spectrum. $x(n)$ is a noise signal obtained by the noise signal obtaining device 20, and is a signal that is roughly correlated with the noise signal included in the electromyography signal $d(n)$. $e(n)$ indicates the filtered electromyography signal. $y(n)$ is an output of the FIR filter 410, and is the estimated noise signal used to remove the noise signal included in the electromyography signal $d(n)$.

The adaptive filter 400 may repeatedly remove the noise signal included in the electromyography signal $d(n)$ by using the noise signal $x(n)$ based on a stochastic gradient descent (SGD) algorithm. At this time, the adaptive filter weights 430 are updated at each step depending on the SGD algorithm.

The FIR filter 410 may filter the noise signal $x(n)$ based on the adaptive filter weights 430.

The subtractor 420 may remove the estimated noise signal $y(n)$ from the electromyography signal $d(n)$.

Hereinafter, a detailed configuration of the noise signal obtaining device 20 will be described with reference to FIGS. 3 to 5.

Figure 3:
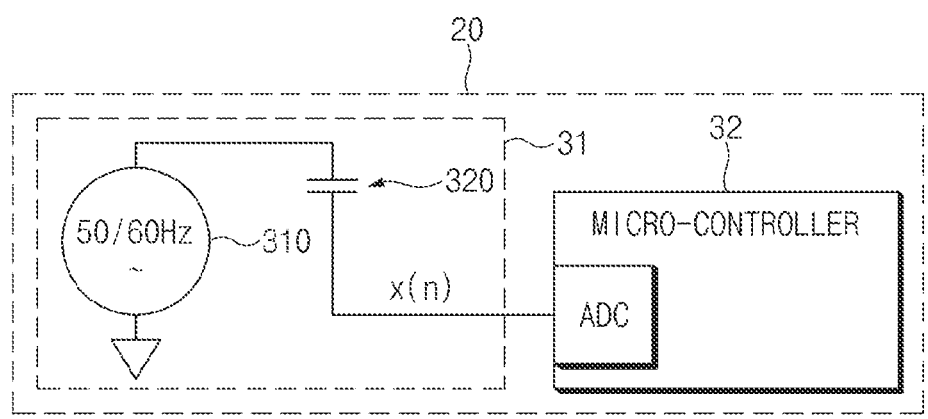
FIG. 3 is a diagram illustrating a detailed configuration of the first scheme of a noise signal obtaining device included in an electromyography signal detection device according to an embodiment of the present disclosure.

FIG. 3 is a diagram illustrating a detailed configuration of the first scheme of a noise signal obtaining device included in an electromyography signal detection device according to an embodiment of the present disclosure.

As illustrated in FIG. 3, the noise signal obtaining device 20 included in an electromyography signal detection device according to an embodiment of the present disclosure may include an antenna 31 and a micro-controller 32.

For example, the antenna 31 may be implemented with a wire. At this time, the length, thickness, and shape of the wire may be adjusted to obtain the noise signal $x(n)$ of a reference frequency (e.g., 50 Hz or 60 Hz). At this time, a noise source 310 of 50 Hz or 60 Hz and a capacitor 320 illustrated inside the antenna 31 indicate the antenna 31 modeled by using a wire.

The micro-controller 32 may obtain the ambient noise signal $x(n)$ with an unknown reference frequency capacitively coupled to a wire through an arbitrary unknown capacitance. At this time, the micro-controller 32 may include an analog-digital converter (ADC), and may receive the noise signal $x(n)$ from the antenna 31 through an ADC channel.

Figure 4:
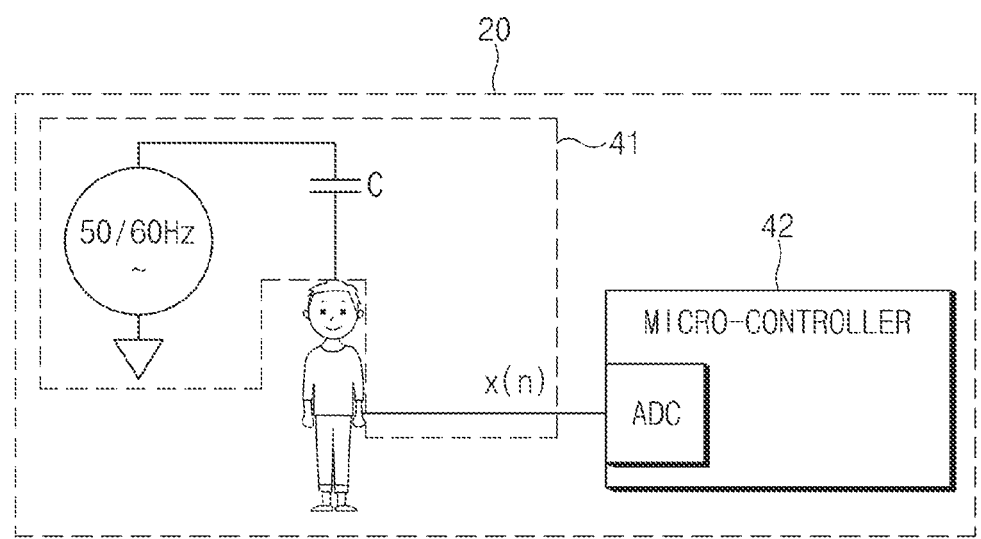
FIG. 4 is a diagram illustrating a detailed configuration of the second scheme of a noise signal obtaining device included in an electromyography signal detection device according to an embodiment of the present disclosure.

FIG. 4 is a diagram illustrating a detailed configuration of the second scheme of a noise signal obtaining device included in an electromyography signal detection device according to an embodiment of the present disclosure.

As illustrated in FIG. 4, the noise signal obtaining device 20 included in an electromyography signal detection device according to an embodiment of the present disclosure may include an antenna 41 and a micro-controller 42.

The electrode is directly connected to the ADC channel of the micro-controller 42 using the antenna 41. At this time, the electrode may be in contact with a user's skin. At this time, a noise source of 50 Hz or 60 Hz and a capacitor C illustrated inside the antenna 41 indicate the antenna 41 modeled by using an electrode attached to the user's skin.

The micro-controller 42 may obtain the ambient noise signal $x(n)$ with an unknown reference frequency (e.g., 50 Hz or 60 Hz with other noise artifacts) capacitively coupled to a human body through a predetermined capacitance. At this time, the micro-controller 42 may include an ADC, and may receive the noise signal $x(n)$ from the antenna 41 through the ADC channel.

Figure 5:
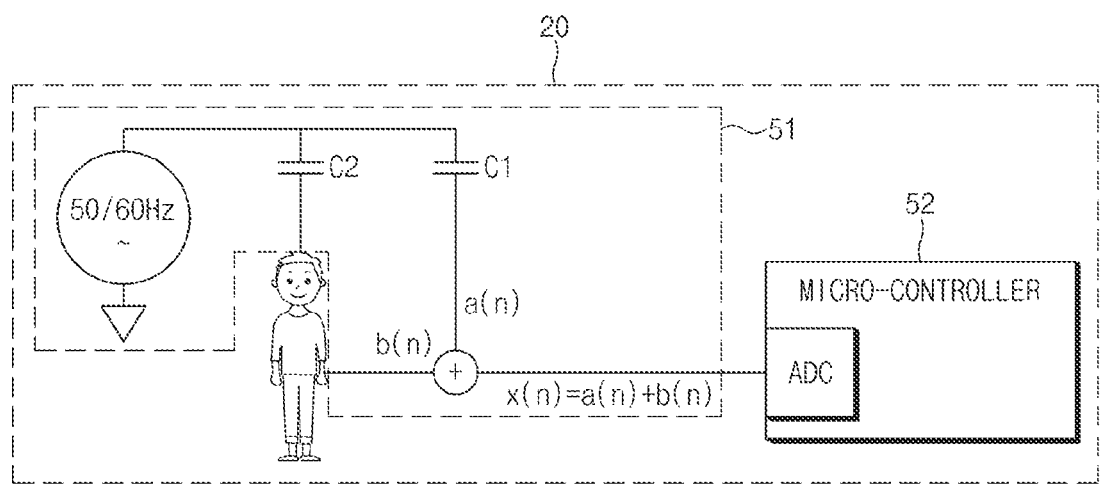
FIG. 5 is a diagram illustrating a detailed configuration of the third scheme of a noise signal obtaining device included in an electromyography signal detection device according to an embodiment of the present disclosure.

FIG. 5 is a diagram illustrating a detailed configuration of the second scheme of a noise signal obtaining device included in an electromyography signal detection device according to an embodiment of the present disclosure.

As illustrated in FIG. 5, the noise signal obtaining device 20 included in an electromyography signal detection device according to an embodiment of the present disclosure may include an antenna 51 and a micro-controller 52.

The antenna 51 may have a shape obtained by combining the antenna 31 modeled by using a wire as illustrated in FIG. 3 and the antenna 41 modeled by using an electrode as illustrated in FIG. 4, and may obtain the noise signal $x(n)$ obtained by combining a noise signal $a(n)$ obtained through the antenna 31 and a noise signal $b(n)$ obtained through the antenna 41.

The micro-controller 52 may obtain the ambient noise signal $x(n)$ by superimposing the noise signal $a(n)$ capacitively coupled to a wire through capacitance C1, and the noise signal $b(n)$ capacitively coupled to a human body through capacitance C2. At this time, the micro-controller 52 may include an ADC, and may receive the noise signal $x(n)$ from the antenna 51 through the ADC channel.

Figure 6A:
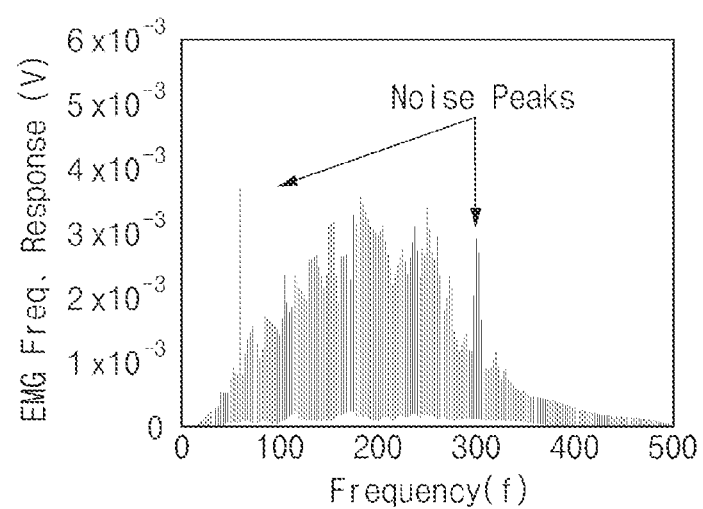
FIGS. 6A to 6C are diagrams illustrating performance of an electromyography signal detection device in the frequency and time domain according to an embodiment of the present disclosure.
Figure 6B:
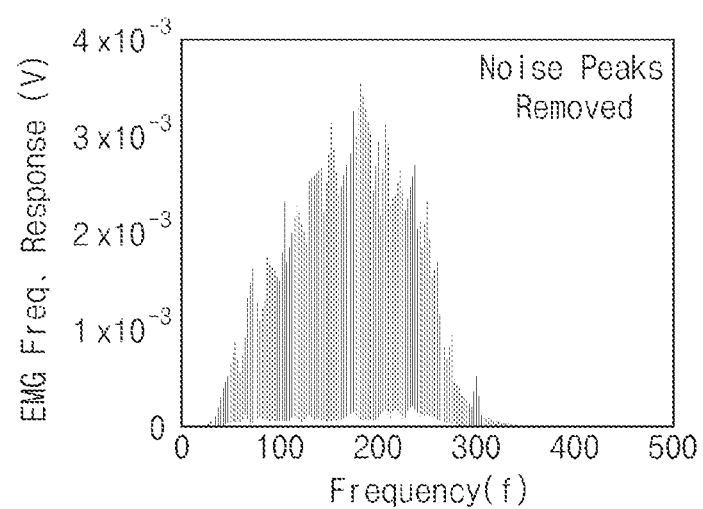
Figure 6C:
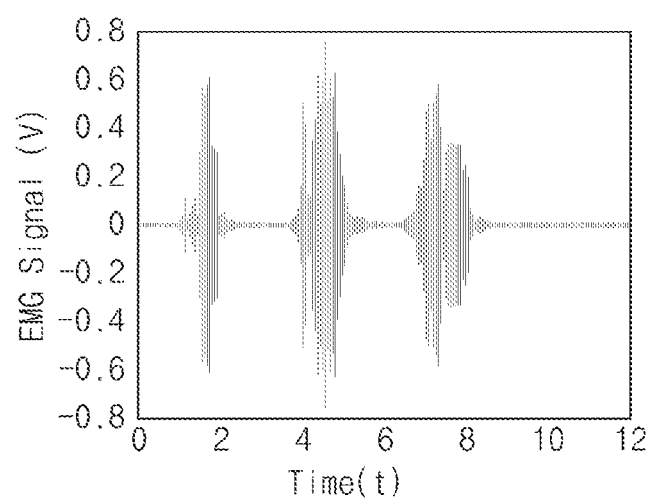

FIGS. 6A to 6C are diagrams illustrating performance of an electromyography signal detection device according to an embodiment of the present disclosure, and illustrate results of analyzing performance in low noise conditions.

A horizontal axis of a graph shown in FIG. 6A indicates a frequency, and a vertical axis of the graph shown in FIG. 6A indicates a voltage of an electromyography signal. The graph shown in FIG. 6A indicates the electromyography signal in a frequency domain that is measured by the electromyography signal acquisition device 30. It may be seen that noise peaks are observed at 60 Hz and 300 Hz, respectively.

FIG. 6B shows a result in which noise peaks are removed from the electromyography signal shown in FIG. 6A by the electromyography signal detection device 100 according to an embodiment of the present disclosure.

FIG. 6C shows a result of displaying the electromyography signal shown in FIG. 6B in a time domain. It may be seen that the electromyography signal is clearly displayed.

Figure 7A:
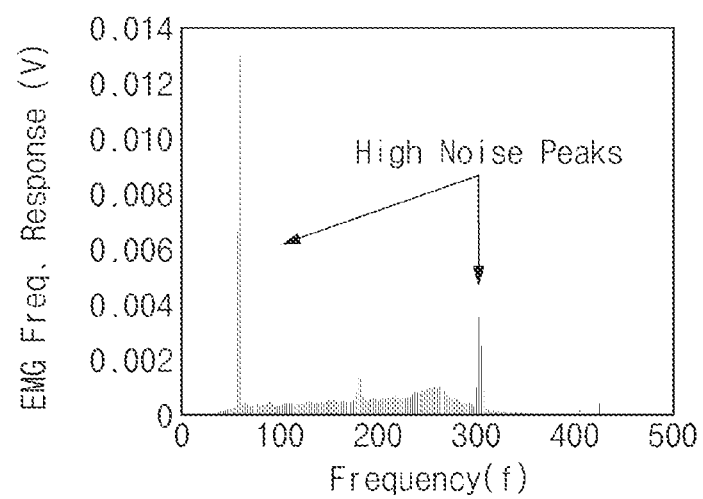
FIGS. 7A to 7C are other additional diagrams illustrating performance of an electromyography signal detection device in the frequency and time domain when there is a high ambient noise presence according to an embodiment of the present disclosure.
Figure 7B:
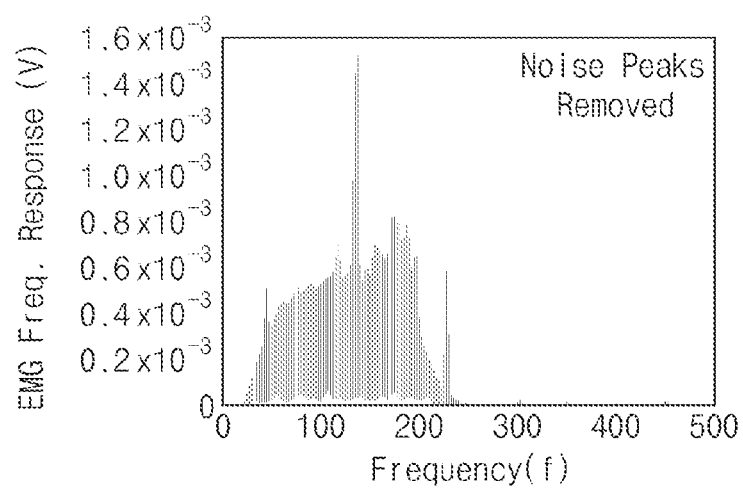
Figure 7C:
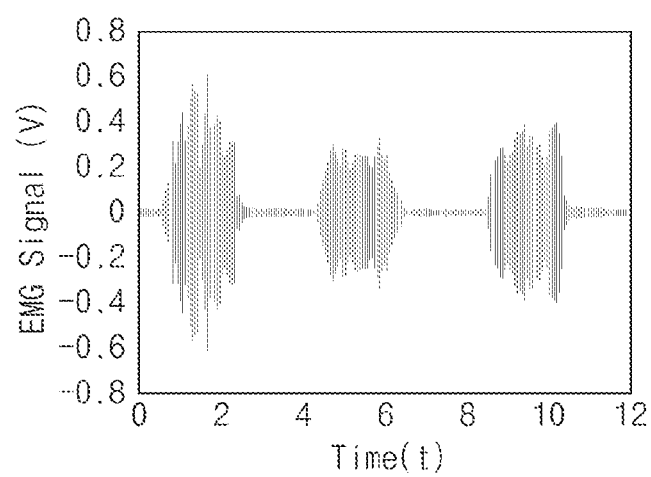

FIGS. 7A to 7C are other diagrams illustrating performance of an electromyography signal detection device according to an embodiment of the present disclosure and illustrate results of analyzing performance in high noise conditions.

A horizontal axis of a graph shown in FIG. 7A indicates a frequency, and a vertical axis of the graph shown in FIG. 7A indicates a voltage of an electromyography signal. The graph shown in FIG. 7A indicates the electromyography signal in a frequency domain that is measured by the electromyography signal acquisition device 30. It may be seen that noise peaks are observed at 60 Hz and its harmonic components of 180 Hz and 300 Hz, respectively.

FIG. 7B shows a result in which noise peaks are removed from the electromyography signal shown in FIG. 7A by the electromyography signal detection device boo according to an embodiment of the present disclosure.

FIG. 7C shows a result of displaying the electromyography signal shown in FIG. 7B in a time domain. It may be seen that the electromyography signal is clearly displayed.

Figure 8:
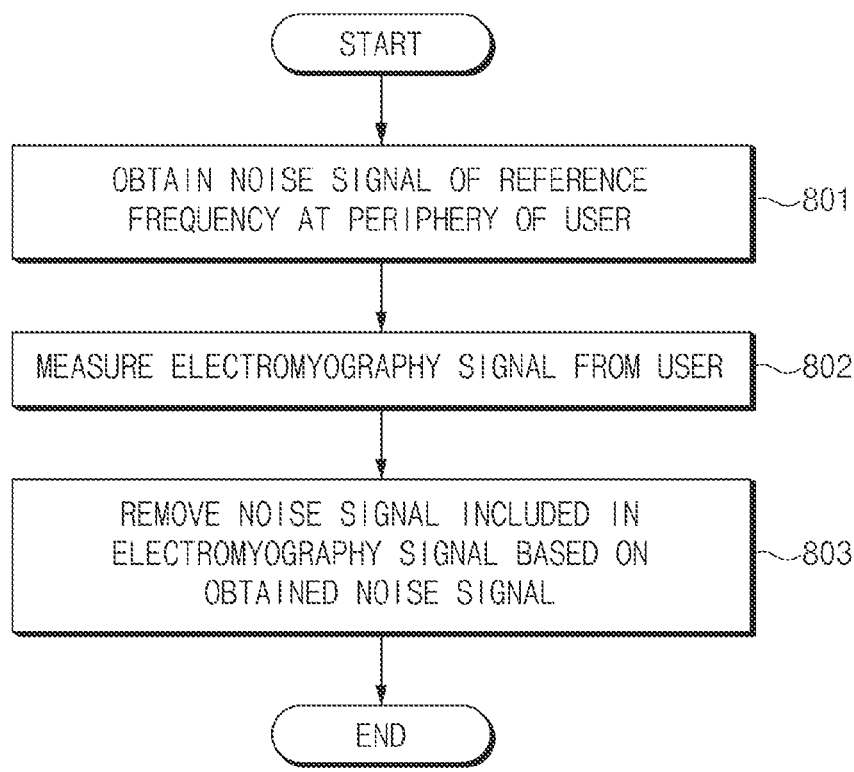
FIG. 8 is a flowchart of an electromyography signal detecting method according to an embodiment of the present disclosure.

FIG. 8 is a flowchart of an electromyography signal detecting method according to an embodiment of the present disclosure.

First of all, the noise signal obtaining device 20 obtains an ambient noise signal with an unknown reference frequency at a periphery of the user (801). The noise signal obtaining device 20 may obtain the noise signal through a scheme which uses a wire which serves the purpose of an antenna, a second scheme using an electrode in contact with a user's skin, and a third scheme which combines the first scheme and the second scheme.

Moreover, the electromyography signal acquisition device 30 measures an electromyography signal from a user (802).

Afterward, the controller 40 removes the noise signal included in the user's electromyography signal based on the noise signal obtained by the noise signal obtaining device 20 (803).

Figure 9:
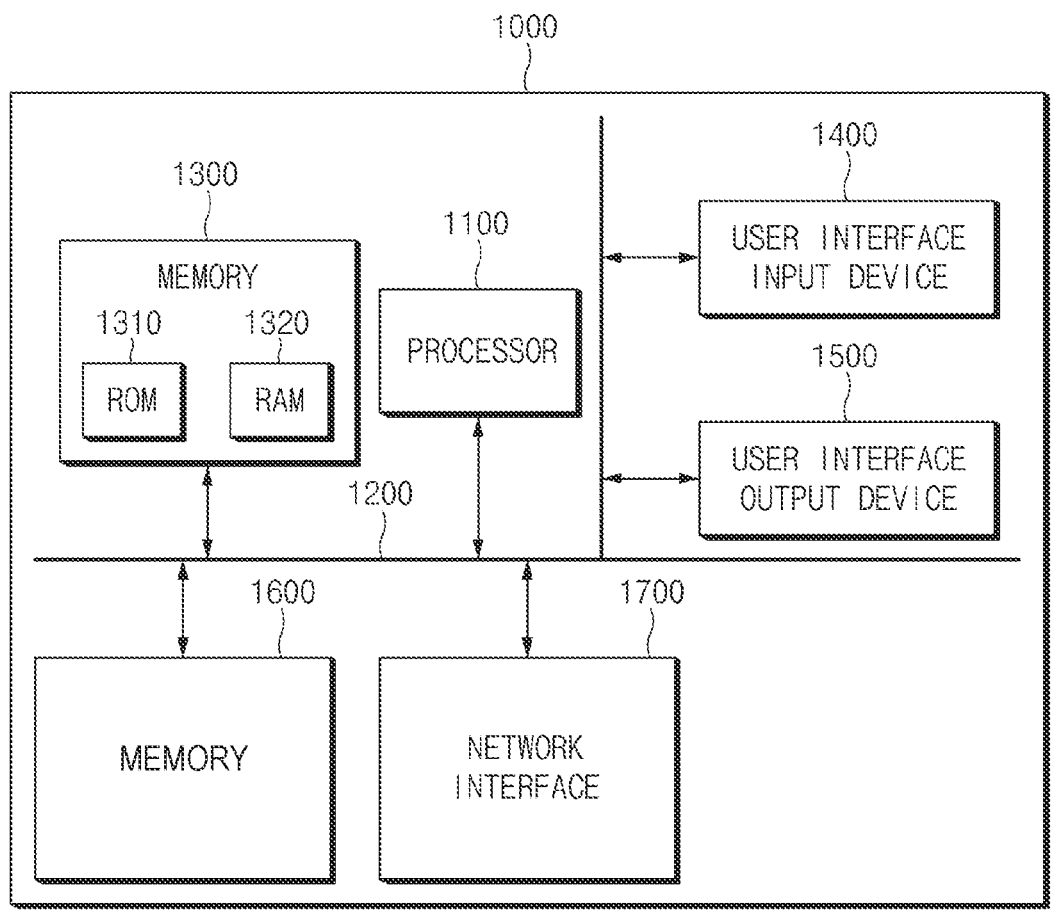
FIG. 9 is a block diagram illustrating a computing system for performing a method of detecting an electromyography signal according to an embodiment of the present disclosure.

FIG. 9 is a block diagram illustrating a computing system for performing a method of detecting an electromyography signal according to an embodiment of the present disclosure.

Referring to FIG. 9, the method of detecting an electromyography signal according to an embodiment of the present disclosure may be implemented through the computing system. A computing system 1000 may include at least one processor 1100, a memory 1300, a user interface input device 1400, a user interface output device 1500, a memory (i.e., a storage) 1600, and a network interface 1700, which are connected with each other through a system bus 1200.

The processor 1100 may be a central processing unit (CPU) or a semiconductor device that processes instructions stored in the memory 1300 and/or the memory 1600. The memory 1300 and the memory 1600 may include various types of volatile or non-volatile storage media. For example, the memory 1300 may include a read only memory (ROM) 1310 and a random access memory (RAM) 1320.

Thus, the operations of the method or the algorithm described in connection with the embodiments disclosed herein may be embodied directly in hardware or a software module executed by the processor 1100, or in a combination thereof. The software module may reside on a storage medium (that is, the memory 1300 and/or the memory 1600) such as a RAM, a flash memory, a ROM, an EPROM, an EEPROM, a register, a hard disk, a solid state drive (SSD), a removable disk, and a CD-ROM. The exemplary storage medium may be coupled to the processor 1100, and the processor 1100 may read information out of the storage medium and may record information in the storage medium. Alternatively, the storage medium may be integrated with the processor 1100. The processor and the storage medium may reside in an application specific integrated circuit (ASIC). The ASIC may reside within a user terminal. In another case, the processor and the storage medium may reside in the user terminal as separate components.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, the representative embodiments of the present disclosure are provided to explain the spirit and scope of the present disclosure, but not to limit them, so that the spirit and scope of the present disclosure is not limited by the embodiments. The scope of the present disclosure should be construed on the basis of the accompanying claims, and all the technical ideas within the scope equivalent to the claims should be included in the scope of the present disclosure.

According to an embodiment of the present disclosure, a device and method for detecting an electromyography signal may detect an electromyography signal with high accuracy by obtaining a noise signal of a reference frequency at a periphery of a user and removing the noise signal included in the user's electromyography signal in an adaptive filtering scheme based on the obtained noise signal.

Hereinabove, although the present disclosure has been described with reference to representative embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An electromyography signal detection device comprising:
    a noise signal obtaining device configured to obtain a noise signal of an unknown reference frequency at a periphery of a user;
    an electromyography signal acquisition device configured to measure an electromyography signal from the user; and
    a controller configured to remove a noise signal included in the electromyography signal of the user based on the obtained noise signal of the unknown reference frequency.

2. The electromyography signal detection device of claim 1, wherein the controller is configured to remove the noise signal included in the electromyography signal of the user by using an adaptive filter.

3. The electromyography signal detection device of claim 1, wherein the noise signal obtaining device is configured to obtain an ambient noise signal of the unknown reference frequency based on a first scheme using a wire as an antenna, a second scheme using an electrode in contact with skin of the user, or a third scheme including a combination of the first scheme and the second scheme.

4. The electromyography signal detection device of claim 3, wherein the noise signal obtaining device is configured to obtain the ambient noise signal of the unknown reference frequency, which is capacitively coupled to the wire, through an arbitrary unknown capacitance.

5. The electromyography signal detection device of claim 4, wherein the noise signal obtaining device is configured to receive the ambient noise signal of the unknown reference frequency from the wire through an analog-digital converter (ADC) channel.

6. The electromyography signal detection device of claim 3, wherein the noise signal obtaining device is configured to obtain the ambient noise signal of the unknown reference frequency, which is capacitively coupled to the skin of the user, through an arbitrary unknown capacitance.

7. The electromyography signal detection device of claim 6, wherein the noise signal obtaining device is configured to receive the ambient noise signal of the unknown reference frequency from the electrode through an analog-digital converter (ADC) channel.

8. The electromyography signal detection device of claim 3, wherein the noise signal obtaining device is configured to obtain a final noise signal with an unknown reference frequency by superimposing a first noise signal capacitively coupled to the wire and a second noise signal capacitively coupled to the skin of the user.

9. The electromyography signal detection device of claim 8, wherein the noise signal obtaining device is configured to receive the final noise signal through an analog-digital converter (ADC) channel.

10. A method of detecting an electromyography signal, the method comprising:
obtaining, by a noise signal obtaining device, a noise signal of an unknown reference frequency at a periphery of a user;
measuring, by an electromyography signal acquisition device, the electromyography signal from the user; and
removing, by a controller, a noise signal included in the electromyography signal of the user based on the noise signal of the unknown reference frequency.

11. The method of claim 10, wherein removing the noise signal included in the electromyography signal of the user includes removing the noise signal included in the electromyography signal of the user by using an adaptive filter.

12. The method of claim 10, wherein obtaining the noise signal of the unknown reference frequency includes obtaining the noise signal of the unknown reference frequency based on a first scheme which uses a wire as an antenna, a second scheme using an electrode in contact with skin of the user, or a third scheme including a combination of the first scheme and the second scheme.

13. The method of claim 12, wherein obtaining the noise signal of the unknown reference frequency includes obtaining an ambient noise signal of an unknown reference frequency, which is capacitively coupled to the wire, through an arbitrary unknown capacitance.

14. The method of claim 13, wherein obtaining the noise signal of the unknown reference frequency further includes receiving the ambient noise signal of the unknown reference frequency from the wire through an analog-digital converter (ADC) channel.

15. The method of claim 12, wherein obtaining the noise signal of the unknown reference frequency includes obtaining the noise signal with the unknown reference frequency, which is capacitively coupled to the skin of the user, through an arbitrary unknown capacitance.

16. The method of claim 15, wherein obtaining the noise signal of the unknown reference frequency further includes receiving the noise signal of the unknown reference frequency from the electrode through an analog-digital converter (ADC) channel.

17. The method of claim 12, wherein obtaining the noise signal of the unknown reference frequency includes obtaining a final noise signal obtained by superimposing a noise signal capacitively coupled to the wire and a noise signal capacitively coupled to the skin of the user.

18. The method of claim 17, wherein obtaining the noise signal of the unknown reference frequency further includes receiving the final noise signal through an analog-digital converter (ADC) channel.

19. A method of detecting an electromyography signal, the method comprising:
obtaining a noise signal of an unknown reference frequency at a periphery of a user;
measuring the electromyography signal from the user; and
removing a noise signal included in the electromyography signal of the user based on the noise signal of the unknown reference frequency.

20. The method of claim 19, wherein removing the noise signal included in the electromyography signal of the user includes removing the noise signal included in the electromyography signal of the user by using an adaptive filter; and
wherein obtaining the noise signal of the unknown reference frequency includes obtaining the noise signal of the unknown reference frequency based on a first scheme which uses a wire as an antenna, a second scheme using an electrode in contact with skin of the user, or a third scheme including a combination of the first scheme and the second scheme.

* * * * *